(12) United States Patent
Fluker

(10) Patent No.: US 6,475,476 B1
(45) Date of Patent: Nov. 5, 2002

(54) HERBAL HAIR TREATMENTS AND METHOD OF MAKING THE SAME

(76) Inventor: Annette Fluker, 30 Summit St., East Orange, NJ (US) 07018

( * ) Notice: Subject to any disclaimer, the term of this patent is extended or adjusted under 35 U.S.C. 154(b) by 0 days.

(21) Appl. No.: 09/718,330

(22) Filed: Nov. 22, 2000

(51) Int. Cl.7 .................................................. A61K 7/06

(52) U.S. Cl. ..................... 424/74; 424/195.17; 424/725; 424/735; 424/746

(58) Field of Search .............................. 424/74, 195.17, 424/725, 735, 746

(56) References Cited

U.S. PATENT DOCUMENTS

| | | | |
|---|---|---|---|
| 4,477,438 A | 10/1984 | Willcockson et al. |
| 4,511,555 A | 4/1985 | Faust |
| 4,658,839 A | 4/1987 | Dallal et al. |
| 5,405,609 A | 4/1995 | Sanchez |
| 5,468,492 A | 11/1995 | Szaloki et al. |
| 5,482,644 A | 1/1996 | Nguyen et al. |

*Primary Examiner*—Russell Travers
*Assistant Examiner*—Alysia Berman

(57) ABSTRACT

A herbal hair treatments and method of making the same for protecting and strengthening hair. The herbal hair treatments and method of making the same includes mixing sage, horsetail, kelp, nettle leaf, horsetail, rosemary and mineral water to form a mixture. Heating the mixture to a full boil. Straining the mixture to form an herb liquid. Mixing into the herb liquid rosemary oil, vitamin E, castor oil and a soap to form a shampoo.

5 Claims, No Drawings

HERBAL HAIR TREATMENTS AND METHOD OF MAKING THE SAME

BACKGROUND OF THE INVENTION

1. Field of the Invention

The present invention relates to hair treatments and more particularly pertains to a new herbal hair treatments and method of making the same for protecting and strengthening hair.

2. Description of the Prior Art

The use of hair treatments is known in the prior art. More specifically, hair treatments heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,477,438; U.S. Pat. No. 5,482,644; U.S. Pat. No. 5,468,492; U.S. Pat. No. 5,405,609; U.S. Pat. No. 4,511,555; and U.S. Pat. No. 4,658,839.

While these devices fulfill their respective, particular objectives and requirements, the aforementioned patents do not disclose a new herbal hair treatments and method of making the same. The inventive device includes mixing sage, horsetail, kelp, nettle leaf, horsetail, rosemary and mineral water to form a mixture. Heating the mixture to a full boil. Straining the mixture to form an herb liquid. Mixing into the herb liquid rosemary oil, vitamin E, castor oil and a soap to form a shampoo.

In these respects, the herbal hair treatments and method of making the same according to the present invention substantially departs from the conventional concepts and designs of the prior art, and in so doing provides an apparatus primarily developed for the purpose of protecting and strengthening hair.

SUMMARY OF THE INVENTION

In view of the foregoing disadvantages inherent in the known types of hair treatments now present in the prior art, the present invention provides a new herbal hair treatments and method of making the same construction wherein the same can be utilized for protecting and strengthening hair.

The general purpose of the present invention, which will be described subsequently in greater detail, is to provide a new herbal hair treatments and method of making the same apparatus and method which has many of the advantages of the hair treatments mentioned heretofore and many novel features that result in a new herbal hair treatments and method of making the same which is not anticipated, rendered obvious, suggested, or even implied by any of the prior art hair treatments, either alone or in any combination thereof.

To attain this, the present invention generally comprises mixing sage, horsetail, kelp, nettle leaf, horsetail, rosemary and mineral water to form a mixture. Heating the mixture to a full boil. Straining the mixture to form an herb liquid. Mixing into the herb liquid rosemary oil, vitamin E, castor oil and a soap to form a shampoo.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new herbal hair treatments and method of making the same apparatus and method which has many of the advantages of the hair treatments mentioned heretofore and many novel features that result in a new herbal hair treatments and method of making the same which is not anticipated, rendered obvious, suggested, or even implied by any of the prior art hair treatments, either alone or in any combination thereof.

It is another object of the present invention to provide a new herbal hair treatments and method of making the same which may be easily and efficiently manufactured and marketed.

It is a further object of the present invention to provide a new herbal hair treatments and method of making the same which is of a durable and reliable construction.

An even further object of the present invention is to provide a new herbal hair treatments and method of making the same which is susceptible of a low cost of manufacture with regard to both materials and labor, and which accordingly is then susceptible of low prices of sale to the consuming public, thereby making such herbal hair treatments and method of making the same economically available to the buying public.

Still yet another object of the present invention is to provide a new herbal hair treatments and method of making the same which provides in the apparatuses and methods of the prior art some of the advantages thereof, while simultaneously overcoming some of the disadvantages normally associated therewith.

Still another object of the present invention is to provide a new herbal hair treatment and method of making the same for protecting and strengthening hair.

Yet another object of the present invention is to provide a new herbal hair treatments and method of making the same which includes mixing sage, horsetail, kelp, nettle leaf, horsetail, rosemary and mineral water to form a mixture. Heating the mixture to a full boil. Straining the mixture to form an herb liquid. Mixing into the herb liquid rosemary oil, vitamin E, castor oil and a soap to form a shampoo.

Still yet another object of the present invention is to provide a new herbal hair treatments and method of making the same that is conveniently used and inexpensively made.

Even still another object of the present invention is to provide a new herbal hair treatment and method of making the same that promotes healthy grooming practices.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying descriptive matter in which there are illustrated preferred embodiments of the invention.

DESCRIPTION OF THE PREFERRED EMBODIMENT

New herbal hair treatments and method of making the same embodying the principles and concepts of the present invention will be described.

The herbal hair treatments and method of making the same generally comprises a hair balm and a shampoo. All ingredients are readily available an no specific brand is required.

The shampoo is prepared by mixing 2 to 4 teaspoons of sage, 2 to 4 teaspoons of horsetail, 2 to 4 teaspoons of kelp, 2 to 4 teaspoons of nettle leaf, 2 to 4 teaspoons horsetail, 2 to 4 teaspoons of rosemary and at least one cup of mineral water to form a mixture. The mixture is then heated to a full boil and strained to leave an herb liquid. To the herbal liquid is added ½ to 2 teaspoon of rosemary oil, ½ to 2 teaspoon of vitamin E, 2 to 4 teaspoons of castor oil and at least ½ cup of a conventional soap to form the shampoo. Ideally, the soap is an almond soap.

The hair balm is prepared by mixing ½ to 2 teaspoon vitamin E liquid, ½ to 2 teaspoon rosemary oil, ½ to 2 teaspoon crystal iodine, ½ to 2 teaspoon wheat germ oil and at least 1 cup of a conventional petroleum jelly to form the hair balm.

In use, a user washes their hair with the shampoo, and thereafter applies the hair balm to their hair. The shampoo and hair balm may also be used independently of each other. The oils and herbs help to protect and strengthen the hair of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of making an herbal hair treatment comprising the steps of:

mixing sage, horsetail, kelp, nettle leaf, rosemary and mineral water to form a mixture;

heating said mixture to a full boil;

straining said mixture to form an herb liquid;

mixing into said herb liquid, rosemary oil, vitamin E, castor oil and a soap to form a shampoo.

2. The method of making an herbal hair treatment as in claim 1, wherein said method comprises:

mixing 3 teaspoons of said sage, 3 teaspoons of said kelp, 3 teaspoons of said nettle leaf, 3 teaspoons of said horsetail, 3 teaspoons of said rosemary and at least one cup of said mineral water to form said mixture;

heating said mixture to a full boil;

straining said mixture to form said herb liquid;

mixing into said herb liquid, 1 teaspoon of rosemary oil, 1 teaspoon of vitamin E, 3 teaspoons of castor oil and ½ cup almond soap to form said shampoo.

3. A method of making an herbal hair treatment comprising the steps of:

mixing vitamin E liquid, rosemary oil, crystal iodine, wheat germ oil and petroleum jelly to form a hair balm.

4. The method of making an herbal hair treatment as in claim 1, wherein said method comprises:

mixing 1 teaspoon of said vitamin E liquid, 1 teaspoon of said rosemary oil, 1 teaspoon of said crystal iodine, 1 teaspoon of said wheat germ oil and 2 cups of said petroleum jelly to form said hair balm.

5. A method of making an herbal hair treatment system comprising the steps of:

mixing 3 teaspoons of sage, 3 teaspoons of kelp, 3 teaspoons of nettle leaf, 3 teaspoons horsetail, 3 teaspoons of rosemary and at least one cup of mineral water to form a mixture;

heating said mixture to a full boil;

straining said mixture to form an herb liquid;

mixing into said herb liquid, 1 teaspoon of rosemary oil, 1 teaspoon of vitamin E, 3 teaspoons of castor oil and ½ cup almond soap to form a shampoo;

mixing 1 teaspoon vitamin E liquid, 1 teaspoon rosemary oil, 1 teaspoon crystal iodine, 1 teaspoon wheat germ oil and 2 cups petroleum jelly to form a hair balm; and wherein a user washes their hair with said shampoo, and wherein said user applies said hair balm to their hair after using said shampoo.

* * * * *